United States Patent [19]

Fagan et al.

[11] Patent Number: 5,269,757
[45] Date of Patent: Dec. 14, 1993

[54] CATHETER WITH INTEGRAL STEERABLE GUIDEWIRE HAVING LINEAR TO ROTARY MOVEMENT

[75] Inventors: John R. Fagan, Pepperell; John A. Wright, Arlington, both of Mass.

[73] Assignee: C. R. Bard, Inc., Murray Hill, N.J.

[21] Appl. No.: 801,449

[22] Filed: Dec. 2, 1991

[51] Int. Cl.⁵ ............................................. A61M 37/00
[52] U.S. Cl. ........................................ 604/95; 604/283
[58] Field of Search ................................. 604/51-53, 604/95, 99, 170, 280, 281, 282, 283; 128/657, 772; 606/192-194, 196

[56] References Cited

U.S. PATENT DOCUMENTS

| | | | |
|---|---|---|---|
| 4,215,703 | 8/1980 | Willson | 128/772 |
| 4,474,174 | 10/1984 | Petruzzi | 128/4 |
| 4,641,654 | 2/1987 | Samson et al. | 604/95 X |
| 4,940,062 | 7/1990 | Hampton et al. | 128/772 |
| 4,941,473 | 7/1990 | Tenerz et al. | 128/637 |
| 5,007,434 | 4/1991 | Doyle et al. | 128/772 |
| 5,054,501 | 10/1991 | Chuttani et al. | 128/772 |
| 5,113,872 | 5/1992 | Jahrmarkt et al. | 128/772 |

FOREIGN PATENT DOCUMENTS

| | | | |
|---|---|---|---|
| 0377453 | 7/1990 | European Pat. Off. | 128/772 |
| 0193885 | 1/1965 | Sweden | 604/95 |

Primary Examiner—John D. Yasko
Assistant Examiner—Adam J. Cermak
Attorney, Agent, or Firm—Morgan & Finnegan

[57] ABSTRACT

A catheter with an integral steerable guidewire converts linear movement of the guidewire to rotational movement at the distal end of the guidewire. The catheter has a guidewire lumen to receive the guidewire. The catheter and guidewire are constructed so that the guidewire can be reciprocated and rotated with respect to the catheter. The guidewire and catheter cooperate in a manner so that when the guidewire is reciprocated axially with respect to the catheter, that axial movement of the guidewire is converted into rotational movement.

16 Claims, 4 Drawing Sheets

CATHETER WITH INTEGRAL STEERABLE GUIDEWIRE HAVING LINEAR TO ROTARY MOVEMENT

FIELD OF THE INVENTION

This invention relates to catheters and guidewires for catheters used in medical procedures.

BACKGROUND OF THE INVENTION

It has been common practice for many years for physicians to use a guidewire as an aid in the placement of a catheter at a selected location in the body of a patient. For example, among the most common uses of guidewires is in the placement of a catheter in a patient's blood vessel to perform a procedure at a specific location in the blood vessel. A number of protocols may be followed. For example, the guidewire first may be inserted into and advanced to the intended vascular site, with the catheter then being loaded onto and advanced along the guidewire to that vascular site. In another technique, the catheter and the guidewire may be assembled before insertion into the patient's vasculature so that they may be navigated together through the patient's blood vessels. In this technique, the distal tip of the guidewire may be permitted to extend slightly out of the distal end of the catheter. The physician can manipulate the guidewire from its proximal end so as to steer the distal end of the guidewire into selected branches of the patient s blood vessels until the intended site of treatment is reached. In another type of catheter, commonly referred to as a fixed wire catheter, the guidewire and catheter are formed as an integral, inseparable unit.

Common to all of the above catheter and guidewire systems is that the steering of the guidewire requires that the physician rotate the guidewire from its proximal end. It is intended in such procedures that the guidewire be sufficiently torsionally rigid to transmit controllably from the proximal to the distal end rotation applied at the proximal end. The rotation, coupled with the curve typically formed in the distal tip of the guidewire enables the guidewire to be selectively steered at blood vessel branches into a selected branch. Thus, by combined pushing and rotational manipulations, the leading, distal tip of the guidewire enables navigation of the guidewire to the site of intended vascular treatment.

Although the technology of small diameter steerable guidewires has developed significantly, the requirement that the distal tip be steered by rotating the guidewire from its proximal end sometimes presents difficulties that may preclude the guidewire from reaching the intended vascular site. In particular, the distal tip of the guidewire may not always follow as precisely as would be desired the rotation applied at the proximal end of the guidewire. This may result from any of a number of reasons. In order to effect rotation of the distal tip, it has been necessary to transmit that rotation controllably along the full length of the guidewire. In many cases, such as in coronary angioplasty procedures, the guidewire is relatively long, extending over approximately 175 cm. The guidewire typically has a diameter of from 0.012" to 0.018". A slight kink or permanent bend in the guidewire will cause it to lose its controllability, that is, the distal tip of a slightly kinked wire may tend to "whip" when the proximal end is rotated. Thus, in a kinked wire, rotation applied at the proximal end of the wire may not be followed with equal movement at the distal end of the wire. Instead, the wire may store the torque applied until it breaks free with the stored torque being released at the distal tip in a rapid rotational whipping of the tip as the stored portion is released.

Another difficulty presented with some types of fixed wire catheters, for example, of the type disclosed in U.S. Pat. No. 4,582,181 is that the guidewire is securely attached to the catheter in the region of the balloon. That tends to further limit the ability to steer the wire and presents an additional problem, that the balloon may become twisted in an hourglass configuration on the wire as the wire is rotated.

The foregoing difficulties with conventional steerable guidewires are accentuated when the guidewire and catheter are to be used in highly tortuous blood vessels, as is often encountered in coronary angioplasty. It would be desirable, therefore, to provide a catheter and guidewire combination which is not encumbered with the foregoing difficulties. It is among the objects of the invention to provide such a system.

SUMMARY OF THE INVENTION

In accordance with the invention, a catheter and guidewire are provided in which the catheter has a guidewire lumen to receive the guidewire. The catheter and guidewire are constructed so that the guidewire can be reciprocated and rotated with respect to the catheter. The distal end of the guidewire protrudes beyond the distal end of the catheter and is formed in a slight curve to facilitate its steerability. The guidewire and catheter are constructed to cooperate in a manner so that when the guidewire is reciprocated axially with respect to the catheter, that axial movement of the guidewire will be converted to rotational movement of the distally protruding end of the guidewire. The conversion of linear to rotational motion is effected by forming the guidewire with an irregularly shaped section that passes through a receptive passage in the guidewire lumen. The irregularly shaped section of the guidewire may be in the form of a twisted ribbon or a helical segment or the like. The passage in the catheter is shaped to engage the irregular section of the guidewire to cause the guidewire to rotate as the guidewire is pushed or pulled through the passage. The linear to rotary motion converter can be located near the distal end of the catheter so that the rotational force is applied to the guidewire near its distal end. Consequently, only a short portion of a guidewire is used to transmit torque to the distal tip and the risk of guidewire whipping is reduced.

It is among the objects of the invention to provide a new system of a catheter and a guidewire for causing rotation of the distal end of the guidewire.

Another object of the invention is to provide a catheter and guidewire combination in which linear movement at the proximal end of the guidewire is converted, at the distal end of the guidewire, to rotational movement.

A further object of the invention is to provide a catheter and steerable small diameter guidewire combination in which the point of application of steering torque to the guidewire is distal of the proximal end of the guidewire.

An additional object of the invention is to provide a new and improved catheter and integral guidewire.

A further object of the invention is to provide a catheter and guidewire combination that avoids the difficulties presented with conventional small diameter steerable guidewires in which rotation is transmitted along the full length of the guidewire.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 1:
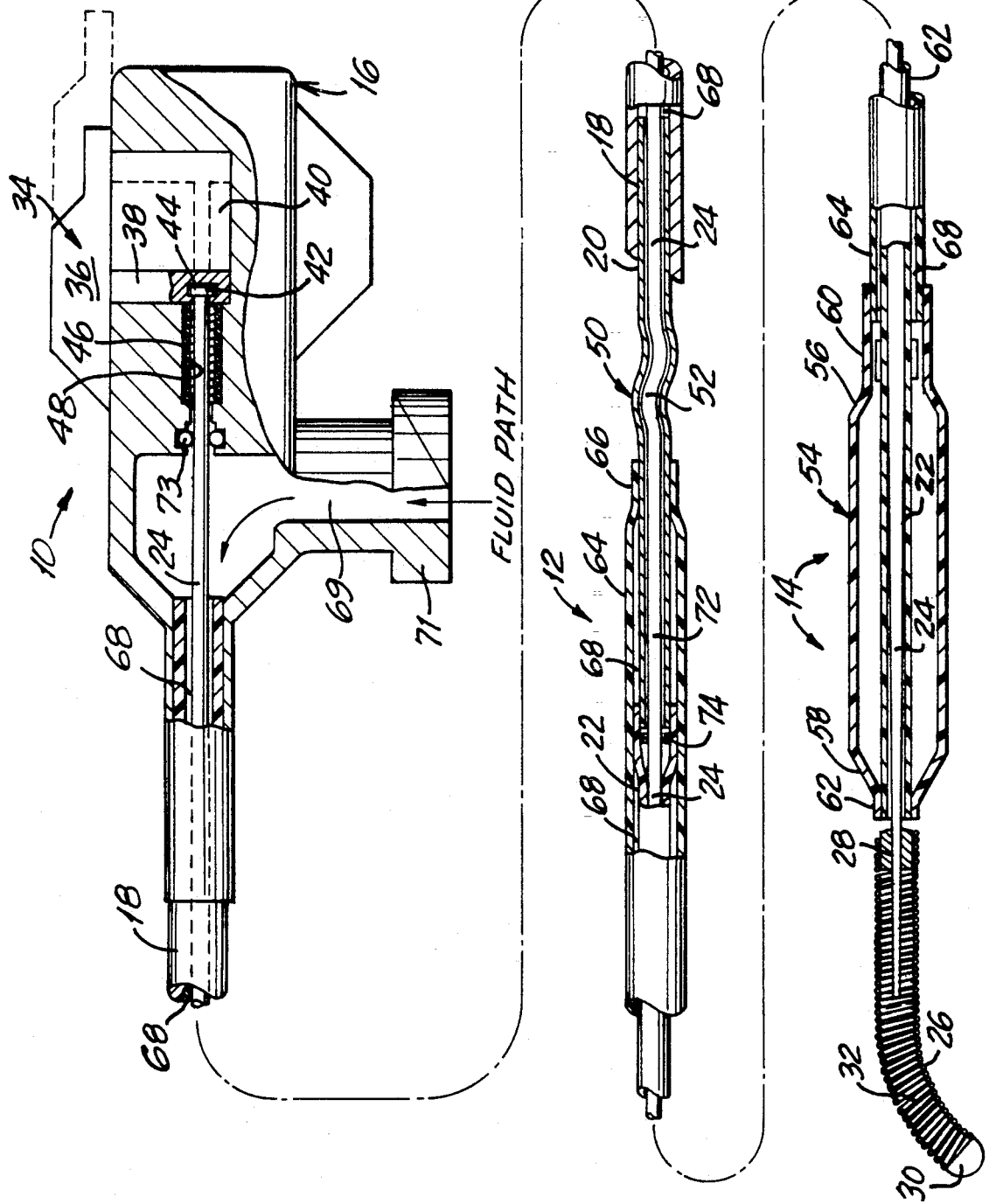
FIG. 1 is a fragmented partly sectional illustration of a catheter and guidewire combination embodying the invention.

FIG. 1 is a fragmented illustration of the catheter showing, in the upper portion of the drawing, the proximal end 10 of the catheter, in the middle portion of the drawing the portion 12 of the catheter and guidewire that include the linear to rotary motion converter and, at the bottom portion 14 of the drawing, the distal end of the catheter and guidewire. The catheter includes a hub 16 at its proximal end and an elongate shaft attached to the hub. The shaft includes a proximal tubular segment 18 which may be formed from stainless steel, an intermediate section 20 that also may be formed from stainless steel tubing and a distal segment 22. Each of the shaft sections 18, 20, 22 is hollow and tubular. The segments 18, 20, 22 are attached to each other end-to-end. Thus, the proximal end of the intermediate segment 20 is received in the lumen at the distal end of the proximal segment 18 and may be attached by conventional means such as brazing. The proximal end of the distal segment 22 is attached to the distal end of the intermediate segment 20 by a suitable adhesive such as a cyanoacrylate adhesive. The distal segment 22 preferably is formed from a suitable polymeric material such as polyimide tubing.

A guidewire 24 is disposed in and extends the length of the lumen defined by the shaft sections 18, 20, 22. The guidewire preferably is formed from stainless steel and is tapered at its distal end so that it will be increasingly flexible in a distal direction. The distal tip of the guidewire protrudes distally beyond the end of the catheter shaft. A helical coil is attached to the distal end of the guidewire, as by solder or by brazing 28. The coil preferably is formed from a highly radiopaque material as is well known in the art to enhance its visibility on a fluoroscope. The distal tip of the coil 26 is provided with a hemispherical bead 30 which may be formed by welding to the tip of the coil. A highly flexible ribbon may extend between the tip of the guidewire shaft 24 and the tip weld 30, the ribbon 32 being welded integrally with the tip weld 30 and attached at the braze 28. The ribbon 32 serves as a safety element in the event that the coil breaks and also facilitates bending the distal tip of the coil into a permanent curve as illustrated in the lower portion of FIG. 1.

The guidewire 24 is connected, at its proximal end, to a slide 34 that is mounted to the hub 16 for slidable movement in a longitudinal direction. The slide 34 includes an externally exposed portion 36 and a depending member 38 which extends into a slot 40 formed in the hub 16. The proximal end of the guidewire shaft 24 is connected to the depending member 38, as by an enlarged element 42 that is received in a slot 44 formed in the depending member 38. The connection between the enlarged element 42 and slot 44 preferably is such as to permit the enlarged element 42 to rotate within the slot 44. The hub is preferably provided with an arrangement to bias the slide 34 and guidewire 24 toward the proximal end of the device and, for that purpose, a helical compression spring 46 is contained in a socket 48 formed in the hub 16. The compression spring 46 surrounds the proximal end of the guidewire shaft 24 and bears against the depending member 38 of the slide 34. The slide 34 is movable between an extended position as shown in solid in FIG. 1 and a retracted position shown in phantom. The compression spring 46 biases the slide in its proximal position so that the guidewire shaft 24 can be extended or retracted lengthwise of the catheter, as determined by the position of the slide. As described below, the intermediate portion of the shaft and a portion of the guidewire 24 received therein are configured to convert the linear motion to rotational motion.

As shown in FIGS. 1 and in enlarged detail in FIGS. 2, 3 and 3A-3C, the device is provided with an arrangement to convert the linear movement of the guidewire to rotational movement. Thus, a portion of the shaft, here illustrated as the intermediate shaft segment 20, is provided with a configuration adapted to cooperate with a mating portion of the guidewire to convert axial movement of the guidewire 24 to rotational movement. In this embodiment, the conversion is achieved by forming a portion of the intermediate segment 20 in a helical configuration, as indicated at 50. A portion of the guidewire, indicated at 52, is provided with a mating helical configuration. As the guidewire 24 is moved longitudinally within the catheter, it will be appreciated that the cooperation of the helical portions 50, 52 of the catheter shaft and guidewire shaft will cause the guidewire shaft to rotate with respect to the catheter. That rotational motion is transmitted to the distal tip of the guidewire and to the helical coil 26. The length and pitch of the helical portions 50, 52 should be selected to permit a full range of angular motion for the guidewire so that the tip of a guidewire can be oriented in any direction.

Figure 3:
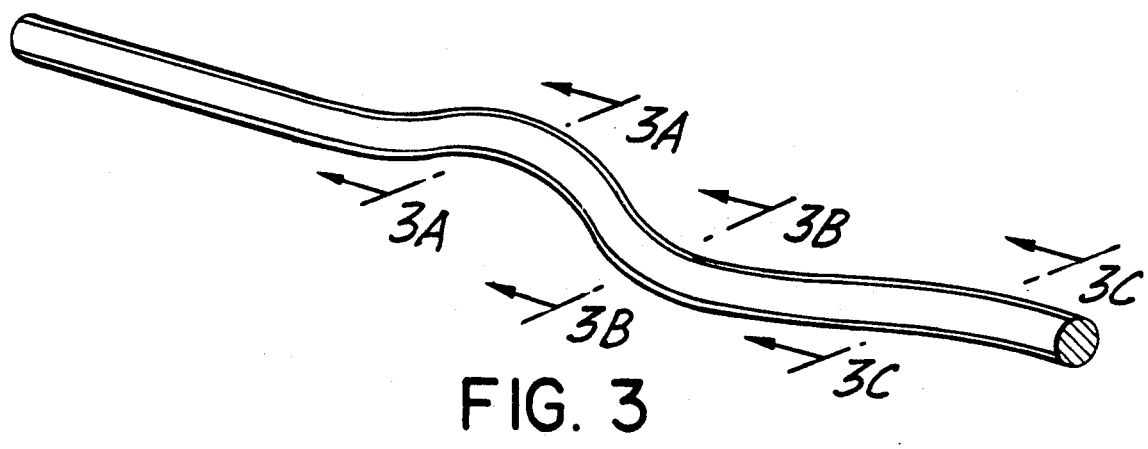
FIG. 3 is an illustration of the portion of the guidewire having a helical irregularity that cooperates with the helically shaped catheter as shown in FIGS. 1 and 2.
Figure 3A:
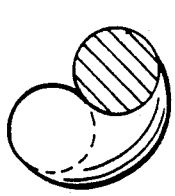
FIG. 3A is a cross-sectional illustration of the guidewire as seen along the line 3A—3A of FIG. 3.
Figure 3B:
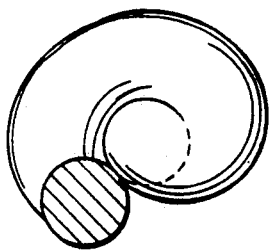
FIG. 3B is a cross-sectional illustration of the guidewire as seen along the line 3B—3B of FIG. 3.
Figure 3C:
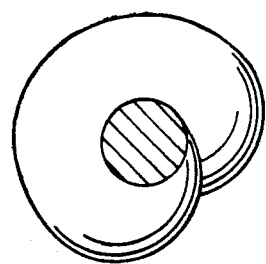
FIG. 3C is a cross-sectional illustration of the guidewire as seen along the line 3C—3C of FIG. 3.
Figure 3D:
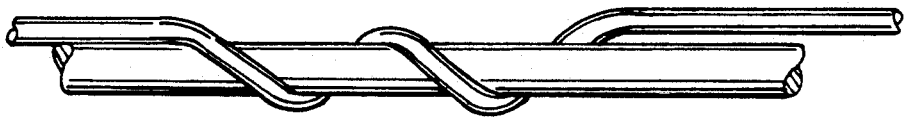
FIG. 3D is a diagrammatic illustration of the manner in which a portion of the guidewire may be formed in a helical configuration.
Figure 4:
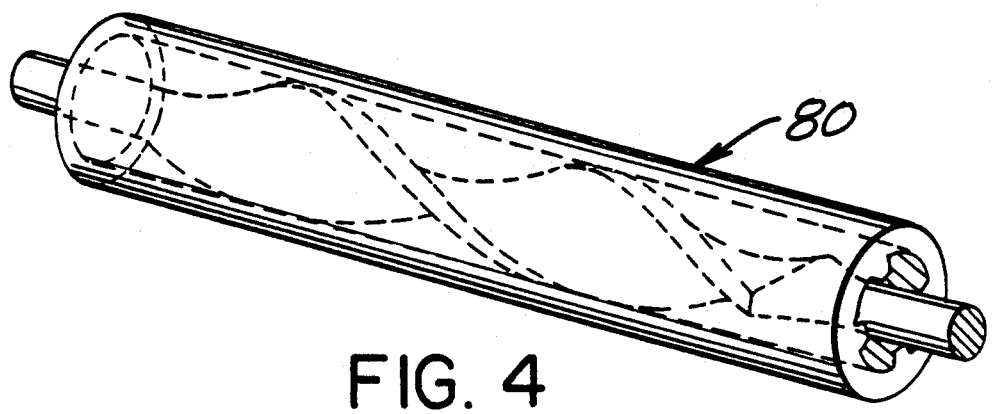
FIG. 4 is an illustration of another embodiment in which the linear to rotary conversion is effected by a twisted ribbon-like guidewire and mated fluted catheter.
Figure 5:
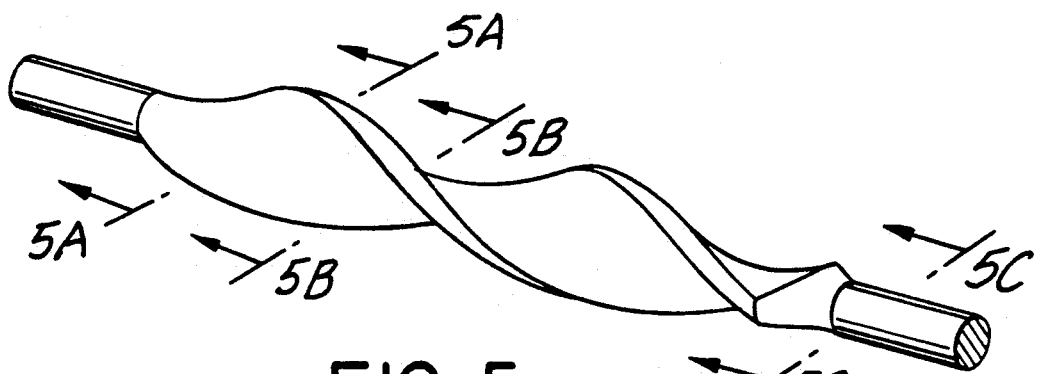
FIG. 5 is an illustration of the irregularly shaped twisted ribbon segment of the guidewire.
Figure 5A:
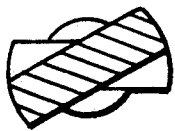
FIG. 5A is a cross-sectional illustration of the twisted ribbon as seen along the line 5A—5A of FIG. 5.
Figure 5B:
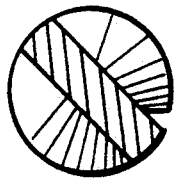
FIG. 5B is a cross-sectional illustration of the twisted ribbon as seen along the line 5B—5B of FIG. 5.
Figure 5C:
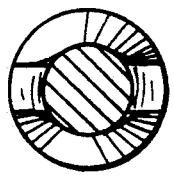
FIG. 5C is a cross-sectional illustration of the twisted ribbon as seen along the line 5C—5C of FIG. 5.

The helical portion 50 in the intermediate segment 20 of the wire may be formed by wrapping the wire helically about a mandrel as suggested in FIG. 3D and, while holding the wire in the helical configuration, applying heat sufficient to relieve the stresses in the helix so that when removed from the mandrel, the treated portion of the wire will retain its helical shape.

The catheter also includes a balloon indicated generally at 54 at the distal end of the catheter. The balloon may be formed from polyethylene terephthalate or other suitable material. The balloon may be formed in the manner described in U.S. Pat. No. 4,490,421 (Levy) to which reference is made and which is hereby incorporated by reference in its entirety. The balloon has proximal and distal cone segments 56, 58 which terminate, respectively, in proximal and distal neck portions 60, 62. The distal neck 62 is attached, as by an adhesive, such as cyanoacrylate to the distal end of the distal segment 22 of the shaft. The proximal neck 60 is attached, also by a suitable adhesive such as cyanoacrylate, to the distal end of a tubular neck extension 64. The neck extension 64 may be formed from a suitable polymeric material, such as polyethylene. The neck extension 64 extends proximally from the balloon over and about the distal end of the intermediate shaft segment 20 and is attached adhesively to the intermediate shaft segment 20 at a connection 66. The neck extension 64 thus surrounds a distal portion of the intermediate shaft segment 20 and a proximal portion of the distal shaft segment 22. The neck extension 64 is dimensioned relative to the intermediate and distal segments 20, 22 of the shaft so as to define an annular inflation lumen 68. The inflation lumen 68 communicates with the interior of the balloon 54. The inflation lumen 68 is in communication with a port 69 in a luer fitting 71 at the proximal end of the device. The luer fitting 71 may be formed integrally with the hub 16. A sliding seal 73, which may be in the form of an O-ring or the like, surrounds the guidewire 24 and permits the guidewire to slide, but in a sealed manner therethrough.

The outer diameter of the guidewire shaft 24 and the inner diameter of the intermediate catheter shaft section 20 provide sufficient clearance for inflation liquid to flow in the annular space defined between the two. In order to communicate the inflation liquid with the portion of the inflation lumen 68 defined by the neck extension 64, one or more ports 72 are formed in the intermediate catheter shaft segment 20, distally of the connection 66 with the neck extension 64. Thus, it will be appreciated that the balloon may be inflated and deflated by connection of a suitable inflation device, such as a syringe, to inject inflation liquid into the balloon through the inflation lumen 68.

Figure 1A:
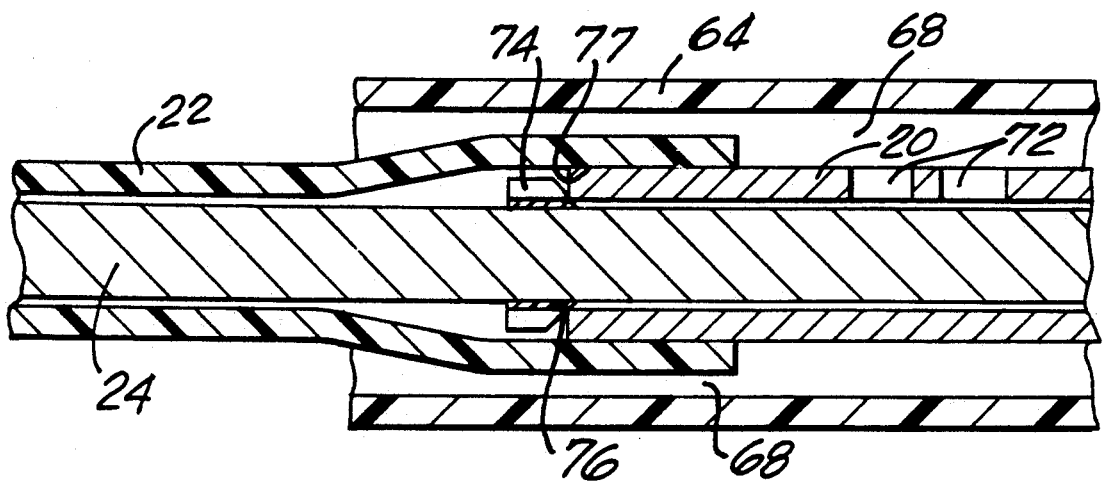
FIG. 1A is an enlarged sectional illustration of the portion of the catheter that includes the distal end of the intermediate shaft and associated sealing ring.
Figure 2:
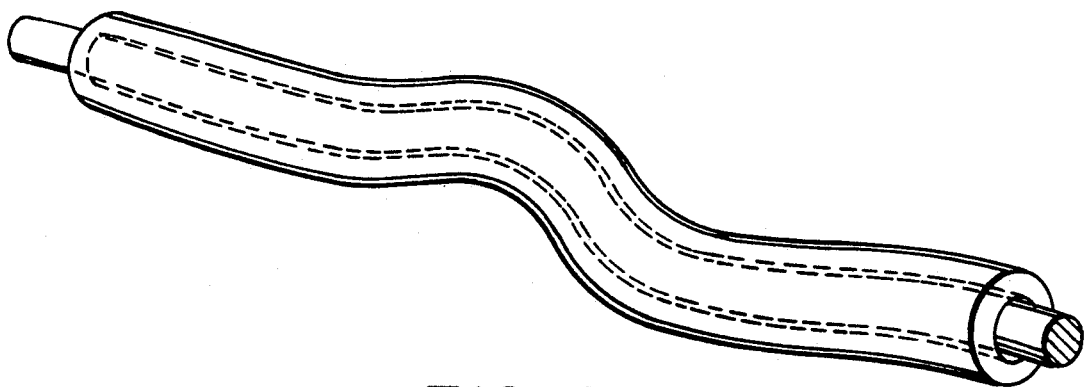
FIG. 2 is an enlarged illustration of that section of the catheter and guidewire in which linear movement is converted to rotational movement.

In order to prevent the inflation liquid from leaking out of the distal end of the intermediate catheter shaft segment 20, a ring seal 74 is attached to and carried by the guidewire shaft 24. The ring seal, shown in enlarged detail in FIG. 1A, may be formed from rubber and is adhesively attached to the guidewire shaft by a suitable adhesive. The ring seal 74 may be formed to include a proximally facing proximally tapering surface 76. The ring seal 74 is located on the guidewire 24 relative to the distal end 77 of the intermediate catheter shaft segment 20 so that when the guidewire 24 is in its retracted, proximal position (FIG. 1A), the ring seal 74 will engage and abut against the distal end 77 of the intermediate catheter shaft segment 20. As illustrated in FIG. 1A the tapered surface 76 may be configured to wedge itself securely in the annular space defined between the guidewire shaft 24 and distal end 77 of the catheter intermediate shaft segment 20. The compression spring 46 at the proximal end of the catheter biases the guidewire 24 in its proximal retracted configuration and, therefore, maintains the ring seal 74 in a normal closed position. Thus, with the guidewire in its proximal retracted position, the balloon may be inflated and deflated by a syringe or other suitable inflation and deflation device connected to the fitting 70.

FIGS. 4, 5 and 5A-5C illustrate an alternate embodiment of the linear to rotary motion converter. In this embodiment, the guidewire is provided with a flat, ribbon like segment 78 that is twisted such that its edges define a helix. The ribbon like segment 78 may be formed as a separate piece, welded to portions of the guidewire shaft at its ends or may be formed directly in the body of the guidewire shaft itself by flattening and twisting a segment of the guidewire. The flat ribbon segment 78 cooperates with a portion of the catheter shaft intermediate segment 80 which is formed to include internal guide members 80 that receive the twisted ribbon segment 78. It will be appreciated from the foregoing that axial movement of the guidewire with respect to the catheter will impart a rotation to the guidewire.

From the foregoing, it will be appreciated that the invention provides a catheter and guidewire system in which the guidewire may be caused to rotate without requiring that the rotation be transmitted along the full length of the guidewire shaft. Rather, the rotational force is imparted to the guidewire at a location that is relatively close to the distal end of the guidewire. Consequently, difficulties that might otherwise result from the use of a guidewire requiring rotational transmission along its full length may be avoided.

It should be understood that the foregoing description of the invention is intended merely to be illustrative thereof and that other embodiments, modifications and equivalents may be apparent to those skilled in the art without departing from its spirit.

Having thus described the invention what I desire to claim and secure by Letters Patent is:

1. A catheter and guidewire for use therewith comprising:
   the catheter having an elongate flexible shaft with proximal and distal ends and at least one lumen extending through the shaft;
   a guidewire having proximal and distal ends and being received in the lumen of the catheter shaft, the guidewire being rotatable and movable lengthwise of the catheter shaft, the distal end of the guidewire protruding distally of the distal end of the catheter shaft;
   each of the guidewire and catheter having cooperative elements engageable with each other to cause the guidewire to rotate with respect to the catheter when the guidewire is moved lengthwise of the catheter, said cooperative elements being disposed closer to the distal end of the catheter than to the proximal end of the catheter.

2. A catheter and guidewire as defined in claim 1 wherein said cooperative elements comprise:
   a portion of each of the lumen and the guidewire being non linear.

3. A catheter and guidewire as defined in claim 2 wherein said non-linear portion is helical.

4. A catheter and guidewire as defined in claim 1 wherein said cooperative elements comprise the guidewire having a flat, twisted portion and the lumen of the catheter shaft having a portion that is narrowed to receive the twisted flat portion and to cooperate therewith to cause rotation of the guidewire in response to linear movement of the guidewire in the catheter.

5. A catheter and guidewire for use therewith comprising:
   the catheter having an elongate flexible shaft with proximal and distal ends and at least one lumen extending through the shaft;
   a guidewire having proximal and distal ends and being received in the lumen of the catheter shaft, the guidewire being rotatable and movable lengthwise of the catheter shaft, the distal end of the guidewire protruding distally of the distal end of the catheter shaft;
   each of the guidewire and catheter having cooperative means for converting linear movement of the guidewire to rotational movement when the guidewire is moved lengthwise of the catheter, said cooperative means being disposed closer to the distal end of the catheter than to the proximal end of the catheter.

6. A catheter and guidewire as defined in either of claims 1 or 5 further comprising:
   a balloon mounted to the distal end of the catheter;
   the catheter including an inflation lumen for communicating the proximal end of the catheter with the interior of the balloon whereby the balloon may be inflated and deflated.

7. A catheter and guidewire as defined in claim 6 further comprising:
   the proximal portion of the catheter having a single lumen that receives the guidewire and defines a portion of the inflation lumen;
   the balloon being mounted on the distal portion of the catheter so that its interior is in communication with the inflation lumen;
   means for effecting a seal between the guidewire and a distal portion of the lumen to prevent leakage of inflation fluid from the inflation lumen.

8. A catheter and guidewire as defined in claim 7 wherein the means for effecting a seal is responsive to the position of the guidewire relative to the catheter to prevent leakage of inflation fluid from the inflation lumen.

9. A catheter and guidewire as defined in claim 8 wherein said seal comprises a resilient ring mounted on the guidewire and engageable with a portion of the inflation lumen.

10. A catheter and guidewire as defined in claim 9 further comprising:
    the catheter shaft having a port located proximally of the balloon;
    a sleeve mounted about the catheter shaft and defining an annular lumen with respect to the catheter shaft, the sleeve having a proximal end that is attached to the catheter shaft and a distal end that is attached to the proximal end of the balloon;
    the catheter shaft having a port communicating the annular portion of the inflation lumen with the more proximal portion of the inflation lumen;
    the resilient ring being mounted on the guidewire at a location distally of the port to effect said seal at a location distally of said port whereby inflation fluid may be caused to flow through the port without leaking from the catheter.

11. A catheter and guidewire as defined in claim 7 further comprising means for biasing the seal toward a sealed configuration.

12. A catheter and guidewire as defined in claim 8 further comprising means for biasing the guidewire in a position as to effect said seal.

13. A catheter and guidewire as defined in claim 9 further comprising means for biasing the guidewire in a position as to effect said seal.

14. A catheter and guidewire as defined in claim 10 further comprising means for biasing the guidewire in a position as to effect said seal.

15. A catheter and integral, non-removable guidewire for use therewith comprising:
    the catheter having an elongate flexible shaft with proximal and distal ends and at least one lumen extending through the shaft;
    an integral guidewire inseparably carried by the catheter, the guidewire having proximal and distal ends and being received in the lumen of the catheter shaft, the guidewire being capable of limited lengthwise movement in the shaft and rotation movement in the shaft, the distal end of the guidewire protruding distally of the distal end of the catheter shaft; and
    means engageable between the catheter and the guidewire for converting linear movement of the guidewire to rotary motion.

16. A catheter and guidewire as defined in claim 15 wherein said converting means is disposed closer to the distal end of the catheter than to the proximal end of the catheter.

* * * * *